US012662487B2

(12) United States Patent
Almario et al.

(10) Patent No.: US 12,662,487 B2
(45) Date of Patent: Jun. 23, 2026

(54) IMIDAZO[1,2-B][1,2,4]TRIAZOL DERIVATIVES FOR USE IN THERAPY

(71) Applicant: SANOFI, Paris (FR)

(72) Inventors: Antonio Almario, Paris (FR); Danielle De Peretti, Paris (FR); Amelie Dommergue, Paris (FR)

(73) Assignee: SANOFI, Paris (FR)

( * ) Notice: Subject to any disclaimer, the term of this patent is extended or adjusted under 35 U.S.C. 154(b) by 366 days.

(21) Appl. No.: 18/578,530

(22) PCT Filed: Jul. 12, 2022

(86) PCT No.: PCT/EP2022/069472
§ 371 (c)(1),
(2) Date: Jan. 11, 2024

(87) PCT Pub. No.: WO2023/285466
PCT Pub. Date: Jan. 19, 2023

(65) Prior Publication Data

US 2024/0300956 A1 Sep. 12, 2024

(30) Foreign Application Priority Data

Jul. 16, 2021 (EP) ..................................... 21305999

(51) Int. Cl.
*C07D 487/04* (2006.01)
*A61K 31/4196* (2006.01)

(52) U.S. Cl.
CPC ........ *C07D 487/04* (2013.01); *A61K 31/4196* (2013.01)

(58) Field of Classification Search
None
See application file for complete search history.

(56) References Cited

U.S. PATENT DOCUMENTS

| | | | | |
|---|---|---|---|---|
| 8,618,301 | B2 * | 12/2013 | Auger | A61P 19/10 546/121 |
| 2004/0010056 | A1 * | 1/2004 | Takahashi | C08K 5/3472 548/335.1 |
| 2013/0123288 | A1 * | 5/2013 | De Peretti | A61P 25/14 546/121 |
| 2024/0294529 | A1 * | 9/2024 | Moulin | C07D 471/14 |

FOREIGN PATENT DOCUMENTS

| | | | |
|---|---|---|---|
| EP | 3701946 | A1 | 9/2020 |
| JP | 3581380 | B2 * | 10/2004 |
| WO | 2009144392 | A1 | 12/2009 |
| WO | 2009144394 | A1 | 12/2009 |
| WO | 2009144395 | A | 12/2009 |
| WO | 2011033230 | A1 | 3/2011 |
| WO | 2023285465 | A1 | 1/2023 |

OTHER PUBLICATIONS

Bogie et al., Research Disclosure, vol. 162, p. 73-75, 1977, Abstract attached (Year: 1977).*

Huang et al., Synthesis of 1H-imidazo[1,2-b]-1,2,4-triazol-6-amines via multicomponent reaction. Mol Divers 11, 73-80 (2007) (Year : 2007).*

Papathoma, Sofia (Authorized Officer), International Search Report and Written Opinion dated Oct. 10, 2022 for International Application No. PCT/EP2022/069472, 11 pages.

Hetzheim et al., "Die Ringumwandlung von 2-Amino-3-phenacyl-1.3.4-oxadiazoliumhalog eniden mit Amidinen21" Hetzheim und Manthey Chem. Ber, Jan. 1, 1970, pp. 2845-2852. Machine translation of Abstract.

Jang et al., "Potent synthetic and endogenous ligands for the adopted orphan nuclear receptor Nurrl", Experimental and Molecular Medicine, vol. 53, No. 1, Jan. 1, 2021, pp. 19-29.

Lesuisse et al., "Development of a novel NURRI/NOT agonist from hit to lead and candidate for the potential treatment of Parkinson's disease", Bioorganic & Medicinal Chemistry Letters, vol. 29, No. 7, Jan. 30, 2019, pp. 929-932.

Papathoma, Sofia (Examiner), Extended European Search Report dated Dec. 1, 2022 for European Patent Application No. 21306000.7, 9 pages.

Database Registry (online), Chemical Abstracts Service, Columbus, Ohio, US, Accession No. 1246550-90-2, Oct. 19, 2010, 1 page.

Papathoma, Sofia (Authorized Officer), International Search Report and Written Opinion dated Oct. 7, 2022 for International Application No. PCT/EP2022/069471, 11 pages.

* cited by examiner

*Primary Examiner* — Jeffrey S Lundgren
*Assistant Examiner* — Anthony Joseph Seitz
(74) *Attorney, Agent, or Firm* — MH2 Technology Law Group, LLP

(57) ABSTRACT

The present invention relates to a compound of the formula (I) or a pharmaceutically acceptable salt thereof: wherein: R1 represents a hydrogen atom, a halogen atom, or a (C1 C4)hydroxyalkyl group, R2 represents a (C1-C6)alkyl group, and R3 represents a hydrogen atom, a (C1-C4)alkyl group or a halogen atom, and Ar represents a divalent aromatic ring or a (C5-C11) heteroarylene group. It further relates to the therapeutic uses thereof, in particular as anticancer agents.

(I)

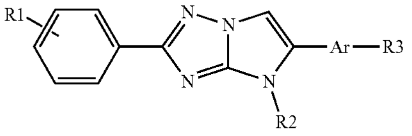

18 Claims, No Drawings

IMIDAZO[1,2-B][1,2,4]TRIAZOL DERIVATIVES FOR USE IN THERAPY

CROSS REFERENCE TO RELATED APPLICATIONS

This application is a U.S. National Stage application of PCT/EP2022/069472 filed on 12 Jul. 2022, which claims benefit of and priority to European Patent Application No. 21305999.1 filed on 16 Jul. 2021, wherein the contents of each application are incorporated herein in their entireties.

FIELD OF INVENTION

Disclosed herein are imidazo[1,2-b][1,2,4]triazol derivatives, the process for their preparation, as well as the therapeutic uses thereof, in particular as anticancer agents, in particular via the modulation of the NR4A subfamily of nuclear receptors, such as Nurr1, also known as NR4A2, NOT, TINUR, RNR-1 or HZF3 and Nur77, also known as NR4A1; also termed Nur77/TR3/NGFIB.

Said derivatives may in particular be useful in the treatment of diseases, such as autoimmunity, cancer, neurodegenerative diseases, cerebral traumas, psychiatric diseases and/or inflammatory diseases, and more particularly cancer.

BACKGROUND

As used herein, Nurr1 and Nur77 are orphan nuclear receptors and respectively pertain to the Nuclear receptor subfamily 4 group A members 2 (NR4A2) and 1 (NR4A1). They are members of the nuclear receptor superfamily and are expressed as early response genes to regulate the expression of multiple target genes.

Nurr1 and Nur77 have the typical structure of a nuclear receptor, including an N-terminal domain, a DNA binding domain, and a ligand-binding domain. They have 90 to 95% homology in their DNA binding domains but are divergent in their N-terminal domains. Their expression and localization are closely associated with their roles in cell proliferation and apoptosis. Moreover, they are also expressed and has a function within the immune system (Front. Immunol., 3 Aug. 2018|https://doi.org/10.3389/fimmu.2018.01797).

Nurr1 codes for a nuclear orphan receptor of the nerve growth factor-induced gene B (NGFI-B) family of transcription factors.

The NR4A subfamily plays a role in metabolic regulation. Nurr1 regulates the expression of multiple genes related to metabolism and gluconeogenesis. Nur77 is involved in lipid and cholesterol metabolism, hepatic steatosis, hepatic gluconeogenesis and islet β-cell proliferation.

The NR4A subfamily also plays a role in regulating the inflammatory response. In particular, Nurr1 have been found to be associated with inflammatory arthritis as well as cartilage and joint inflammation.

The activity of Nurr1 and Nur77 in cancer, regulated by various cellular signaling pathways, has also been demonstrated. For example, the expression of Nurr1 has been linked to colorectal cancer and Nur77 is overexpressed in colon, lung and breast cancers. The dysregulation of both Nurr1 and Nur77 expression may also be a contributing factor in tumorigenesis.

The NR4A subfamily is also related to nerve and neurological diseases. In particular, Nurr1 is involved in the regulation of several physiological functions of the human central nervous system such as memory and learning with a proven activity in dopamine synthesis and metabolism.

Nur77 is expressed in various regions in the brain and its overexpression improves oxygen and glucose deprivation-induced neural damage, while its knockdown exacerbates these conditions. Both Nurr1 and Nur77 have in particular been linked to Parkinson's disease.

Some compounds are already known to regulate Nur77 but further investigations are needed for identifying compounds modulating Nurr1 and Nur77 as well as their therapeutic activity.

There is a permanent need to find new compounds having a Nur77- and/or Nurr1-modulating effect. There is in particular a need to find new treatments for cancer, and specifically targeted therapies used to attack tumor cells with reduced effects on healthy cells.

SUMMARY OF THE INVENTION

The inventors have now found that the compounds as defined in formula (I) hereinafter have a Nur77- and Nurr1-modulating effect.

Said compounds of formula (I) may thus be useful in the treatment and/or prevention of treatment and prevention of diseases, such as autoimmune disorders, cancer, neurodegenerative diseases, cerebral traumas, psychiatric diseases and/or inflammatory diseases.

According to a first aspect, the present invention therefore relates to a compound of formula (I) as defined below, or any one of its pharmaceutically acceptable salts.

Herein is further provided a compound of formula (I) as defined below, for use as a medicament.

Herein is also provided a compound of formula (I) as defined below, for use in the treatment and/or prevention of autoimmune disorders, cancer, neurodegenerative diseases, cerebral traumas, psychiatric diseases and/or inflammatory diseases, more particularly of cancer. A compound of formula (I) could also be used as a treatment associated with stem cell transplants and/or grafts.

Herein is also provided a compound of formula (I) as defined below, for use in the treatment and/or prevention of neurodegenerative diseases, cerebral traumas, psychiatric diseases and/or inflammatory diseases.

Herein is also provided a compound of formula (I) as defined below, for use in the treatment and/or prevention of autoimmune disorders and cancers.

Herein is also provided the use of a compound of formula (I) as defined below for the manufacture of a medicament, in particular a medicament for the treatment and/or prevention of autoimmune disorders, cancer, neurodegenerative diseases, cerebral traumas, psychiatric diseases and/or inflammatory diseases, more particularly of cancer.

Herein is finally provided a pharmaceutical composition comprising a compound of formula (I), or any one of their pharmaceutically acceptable salts, and at least one pharmaceutically acceptable excipient, for use in the treatment and/or prevention of autoimmune disorders, cancer, neurodegenerative diseases, cerebral traumas, psychiatric diseases and/or inflammatory diseases, more particularly of cancer.

In particular, the invention relates to a medicament comprising a compound of formula (I) or any one of their pharmaceutically acceptable salts, for use in the treatment and/or prevention of autoimmune disorders, cancer, neurodegenerative diseases, cerebral traumas, psychiatric diseases and/or inflammatory diseases, more particularly of cancer.

Definitions

As used herein, the term "patient" refers to either an animal, such as a valuable animal for breeding, company or preservation purposes, or preferably a human or a human child, which is afflicted with, or has the potential to be afflicted with, one or more diseases described herein.

In particular, as used in the present application, the term "patient" refers to a mammal such as a rodent, cat, dog, primate or human, preferably said subject is a human.

The identification of those patients who are in need of treatment of herein-described diseases is well within the ability and knowledge of one skilled in the art. A veterinarian or a physician skilled in the art can readily identify, by the use of clinical tests, physical examination, medical/family history or biological and diagnostic tests, those patients who are in need of such treatment.

In the context of the invention, the term "treating" or "treatment", as used herein, means preventing, reversing, alleviating, inhibiting the progress of, or preventing the disease and its resulting cognitive, motor or metabolic changes.

Therefore, the term "treating" or "treatment" encompasses within the framework of the present invention the improvement of medical conditions of patients suffering from the diseases as described herein, in particular in the paragraph "PATHOLOGIES".

As used herein, an "effective amount" refers to an amount of a compound of the present invention which is effective in preventing, reducing, eliminating, treating or controlling the symptoms of the herein-described diseases.

The term "controlling" is intended to refer to all processes wherein there may be a slowing, interrupting, arresting, or stopping of the progression of the diseases described herein, but does not necessarily indicate a total elimination of all disease and condition symptoms, and is intended to include prophylactic treatment.

The term "effective amount" includes "prophylaxis-effective amount" as well as "treatment-effective amount".

The term "preventing", as used herein, means reducing the risk of onset or slowing the occurrence of a given phenomenon, namely in the present invention, a disease as described herein.

As used herein, "preventing" also encompasses "reducing the likelihood of occurrence" or "reducing the likelihood of reoccurrence".

The term "prophylaxis-effective amount" refers to a concentration of compound of this invention that is effective in inhibiting, preventing, decreasing the likelihood of occurrence of anyone of the herein described diseases.

Likewise, the term "treatment-effective amount" refers to a concentration of compound that is effective in treating the herein described diseases.

As used herein, the term "pharmaceutically acceptable" refers to those compounds, materials, excipients, compositions or dosage forms which are, within the scope of sound medical judgment, suitable for contact with the tissues of human beings and animals without excessive toxicity, irritation, allergic response or other problem complications commensurate with a reasonable benefit/risk ratio.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. Pharmaceutically acceptable salts of the compounds of this invention include those derived from suitable inorganic and organic acids and bases as it will be apparent from the below detailed description.

The term "pharmaceutically acceptable carrier, adjuvant, or vehicle" may refer to any pharmaceutically acceptable excipient, such as a non-toxic carrier, adjuvant, or vehicle that does not destroy the pharmacological activity of the compound with which it is formulated.

DETAILED DESCRIPTION OF THE INVENTION

Compounds of Formula (I)

The inventors have surprisingly found that the compounds of formula (I) as disclosed herein after are useful for preventing and/or treating of autoimmune disorders, cancer, neurodegenerative diseases, cerebral traumas, psychiatric diseases and/or inflammatory diseases, more particularly of cancer.

Thus, according to a first aspect, a subject-matter of the present invention relates to a compound of formula (I), or a pharmaceutically acceptable salt thereof:

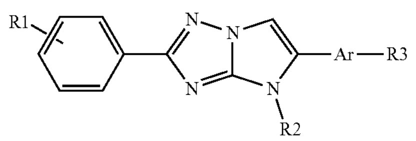

(I)

wherein:

- R1 represents a hydrogen atom, a halogen atom, or a $(C_1\text{-}C_4)$hydroxyalkyl group,
- R2 represents a $(C_1\text{-}C_6)$alkyl group,
- R3 represents a hydrogen atom, a $(C_1\text{-}C_4)$alkyl group or a halogen atom, and
- Ar represents a divalent aromatic ring or a $(C_5\text{-}C_{11})$ heteroarylene group.

In the context of the present invention, the term:

- "halogen" is understood to mean chlorine, fluorine, bromine, or iodine, and in particular denotes chlorine, fluorine or bromine, preferably fluorine;
- "$(C_1\text{-}C_x)$alkyl", as used herein, respectively refers to a $C_1\text{-}C_x$ normal, secondary or tertiary monovalent saturated, linear or branched, hydrocarbon radical, for example $(C_1\text{-}C_6)$alkyl. Examples are, but are not limited to, methyl, ethyl, propyl, n-propyl, isopropyl, butyl, isobutyl, sec-butyl, tert-butyl, pentyl, isopentyl, hexyl and isohexyl groups, and the like;
- an aromatic ring means, according to Hückel's rule, that a molecule has 4n+2 π-electrons. According to one embodiment, a divalent aromatic ring is a phenylene group.
- a $(C_5\text{-}C_{11})$heteroarylene group, as used herein, refers to a divalent monocyclic aromatic group or to a divalent bicyclic aromatic group where at least one of the ring is aromatic and wherein one to three ring carbon atom is replaced by a heteroatom, such as nitrogen, oxygen or sulphur. By way of examples of heteroaryl groups, mention may be made of, but not limited to the divalent group corresponding the following heteroaryls: oxazole, isoxazole, pyridine, pyrimidine, pyridazine, triazine, pyrazine, oxadiazole, furane, pyrazole, thiazole, isothiazole, thiadiazole, imidazole, triazole, indole and the like. In the framework of the present invention, the heteroarylene group is advantageously an indolylene group.

The compounds of formula (I) can exist in the form of pharmaceutically acceptable salts, such salts being part of the invention; these salts can be prepared with pharmaceutically acceptable acids, such as trifluoroacetic acid (P. Stahl, C. Wermuth; Handbook of pharmaceutical salts; Wiley Ed.), but other salts, obtained, for example, for the purification or isolation of the compounds of formula (I), are part of the invention.

In particular, "Pharmaceutically acceptable salt" refers to inorganic and organic acids addition salts.

The compounds of formula (I) or any of their pharmaceutically acceptable salts may form solvates or hydrates, and the invention includes all such solvates and hydrates.

The terms "hydrates" and "solvates" simply mean that the compounds (I) according to the invention can be in the form of a hydrate or solvate, i.e. combined or associated with one or more water or solvent molecules. This is only a chemical characteristic of such compounds, which can be applied for all organic compounds of this type.

In an embodiment, in the compound of formula (I) as defined above,

R1 is a halogen atom, in particular a fluorine atom, or a $—CH_2OH$ group,

R2 and R3 are as defined above, and

Ar is a phenylene group or an indolylene group.

In another embodiment, in the compounds of formula (I) as defined above,

R2 is a methyl group, and

R3 is a hydrogen atom or a fluorine atom.

In another embodiment, the compound of formula (I) is selected from the following compounds or a pharmaceutically acceptable salt thereof, in particular trifluoroacetate salt thereof:

(1)

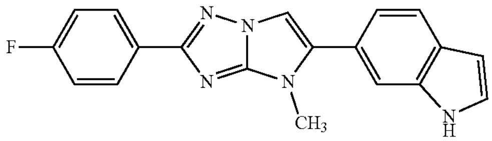

(2)

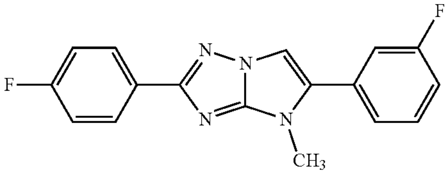

(3)

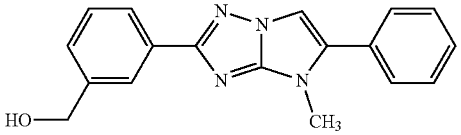

and or a pharmaceutically acceptable salt thereof.

The compound of formula (I) below (1)

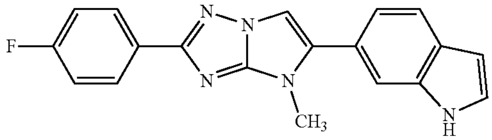

is also called 6-[2-(4-fluorophenyl)-4-methyl-imidazo[1,2-b][1,2,4]triazol-5-yl]-1H-indole and herein after called compound (1).

The compound of formula (2) below (2)

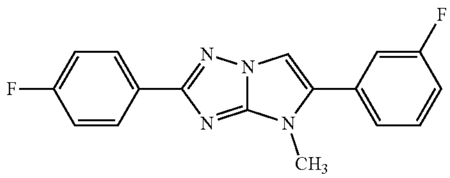

is also called 5-(3-fluorophenyl)-2-(4-fluorophenyl)-4-methyl-4H-imidazo[1,2-b][1,2,4]triazole.

The compound of formula (3) below (3)

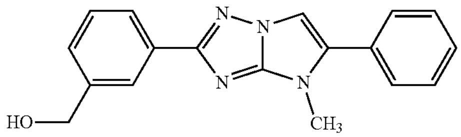

is also called [3-(4-methyl-5-phenyl-4H-imidazo[1,2-b][1,2,4]triazol-2-yl)phenyl]methanol.

The compounds of the formula (I) can be prepared by conventional methods of organic synthesis practiced by those skilled in the art.

The man skilled in the art may, for instance, refer to the content of WO2009/144392.

The compounds of the formula (I) and other related compounds having different substituents are synthesized using techniques and materials described below or otherwise known by the skilled person in the art. In addition, solvents, temperatures and other reaction conditions presented below may vary as deemed appropriate to the skilled person in the art.

General below methods for the preparation of compounds of formula (I) may be optionally modified by the use of appropriate reagents and conditions for the introduction of the various moieties found in the formula (I) as described below.

Scheme 1 preparation of Compound (I)

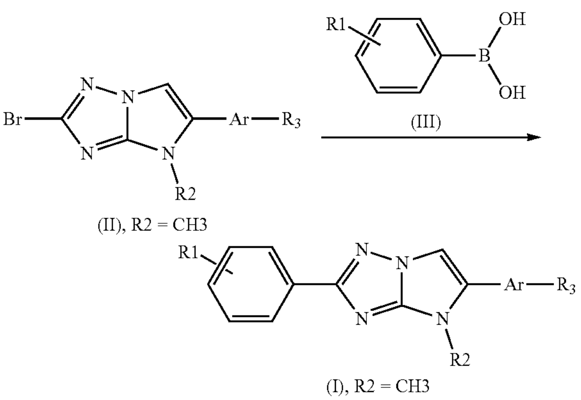

According to scheme 1, in which Ar, R1 and R3 are as defined above, a compound of formula (II) may be reacted with a catalyst, such as a palladium catalyst, for example:

palladium acetate in a solvent such as toluene, in the presence of 2-dicyclohexylphosphino-2',6'-dimethoxy-1,1'-biphenyl in particular under inert atmosphere, for example under argon, or tetrakis(triphenylphosphin)palladium(0), in acetonitrile and toluene, in the presence of a compound of formula (III)

(III)

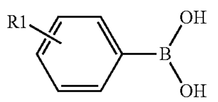

in which R1 is as defined above. The reaction may then be heated up to reflux of solvent, in presence of a base such as $K_3PO_4$ or $Na_2CO_3$ to give the compound of formula (I).

When Ar is an indenylene group, then the N atom can be protected by a phenylsulphonyl group or a tosylate group during all the reactions steps as described herein, as for intermediate compounds (IIa) and (IVa) as described herein after.

The compound of formula (II) allowing the obtention of compound (1) is called 1-(benzenesulfonyl)-6-(2-bromo-4-methyl-imidazo[1,2-b][1,2,4]triazol-5-yl)indole (compound (IIa)).

The compound of formula (II) allowing the obtention of compound (2) is called 2-bromo-5-(3-fluorophenyl)-4-methyl-4H-imidazo[1,2-b][1,2,4]triazole (compound (IIb)), The compound of formula (II) allowing the obtention of compound (3) is called 2-bromo-4-methyl-5-phenyl-4H-imidazo[1,2-b][1,2,4]triazole (compound (IIc)), The compound of formula (II) may be prepared according to scheme 2 below.

Scheme 2

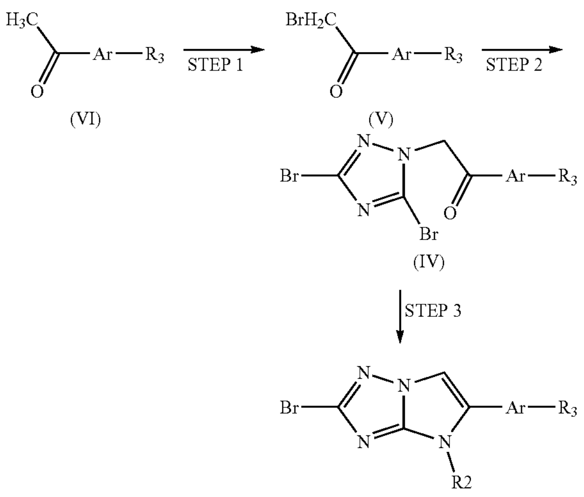

(VI) (V) (IV) (II)

According to scheme 2, in which Ar, R2 and R3 are as defined above, a compound of formula (VI) may be mixed in STEP 1 with a solution brought to reflux comprising a metal bromide, such a copper bromide in a solvent such as ethyl acetate. Said step is described in WO2009/144392, page 38, point 6.4. The mixture may be brought to reflux for example for 3 to 6 hours for obtaining a compound of formula (V), wherein R3 is as defined above. After this STEP 1, STEP 2 may be performed in mixing said compound of formula (V) with 3,5-dibromo-1,2,4-triazole in a solvent such as dichloromethane, dimethylformamide or dimethyl sulfoxide, the mixture being stirred for example during 10 to 20 hours at room temperature to give a compound of step (IV) wherein Ar and R3 are as defined above.

STEP 3 allows the formation of compound (II) by reacting a compound of formula (IV) as obtained in STEP 2, in a solvent such as toluene, benzene or dichloromethane, in presence of a solution comprising an amine of the formula $H_2NR2$, wherein R2 is a $(C_1$-$C_6)$alkyl group, for example at a temperature ranging from 120 to 160° C., in particular during 20 to 30 hours.

Thus, herein is also provided a process for preparing a compound of formula (II) as described above, wherein a compound of formula (IV)

(IV)

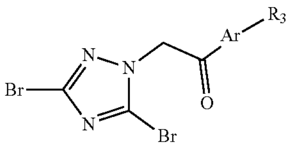

wherein Ar and R3 are as defined above, is reacted with an amine of the formula $H_2NR_2$, wherein R2 is defined above, for example in a solvent such as toluene, benzene or dichloromethane and for example at a temperature ranging from 120 to 160° C., in particular during 20 to 30 hours.

The compound of formula (IV) allowing the obtention of compound (1) is called 1-[1-(benzenesulfonyl)indol-6-yl]-2-(3,5-dibromo-1,2,4-triazol-1-yl)ethenone (compound (IVa)).

The compound of formula (V) allowing the obtention of compound (1) is called 2-bromo-1-[1-(phenylsulphonyl)indol-6-yl]ethanone.

The compound of formula (VI) allowing the obtention of compound (1) is called 6-acetyl-1-(phenylsulphonyl)indole.

The compound of formula (VI) may be prepared according to scheme 3 below.

Scheme 3

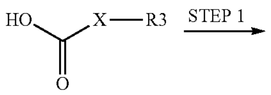

(IX)

-continued

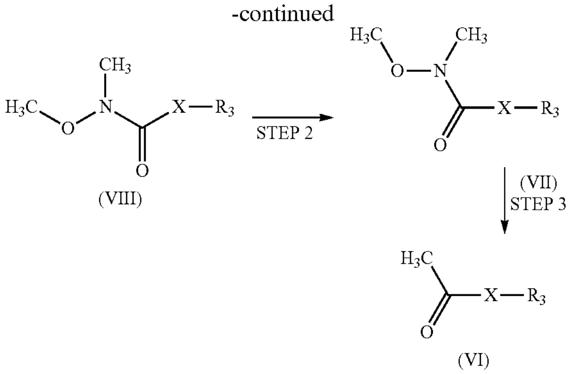

According to scheme 3, in which R3 is as defined above, STEP 1 to 3 may be performed according to WO2009/144392, page 37, points 6.1 to 6.3.

Compounds of formula (VIII) and (IX) are commercially available or may be afforded according to methods known to the man skilled in the art.

Herein is also provided a process for preparing a compound of formula (I) as described above, wherein a compound of formula (II)

(II)

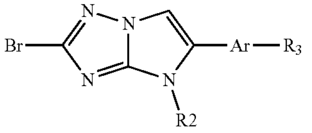

wherein Ar, R2 and R3 are as defined above, is reacted with a catalyst, such as a palladium catalyst, for example:

palladium acetate in a solvent such as toluene, in the presence of 2-dicyclohexylphosphino-2',6'-dimethoxy-1,1'-biphenyl in particular under inert atmosphere, for example under argon, or tetrakis(triphenylphosphin)palladium(0), in acetonitrile and toluene, in the presence of a compound of formula (III)

(III)

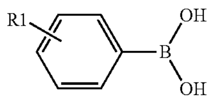

in which R1 is as defined above.

Herein are also provided the intermediate compounds selected from the compounds of formula (IIa) and (IVa)

(IIa)

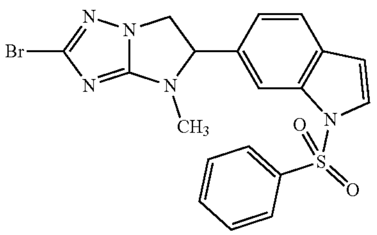

-continued (IVa)

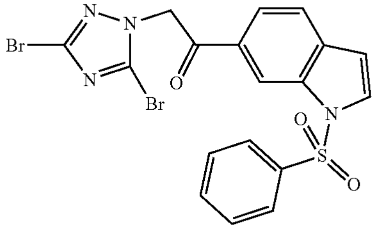

Pathologies

As used herein, "cancer", and unless stated otherwise, may relate to any disorder associated with abnormal cell growth, which thus includes malignant tumors and benign tumors, metastatic tumors and non-metastatic tumors, solid tumors and non-solid tumors. In particular, it encompasses metastases and/or dysplasia as well as a pre-cancerous condition, an early-stage cancer or a non-metastatic cancer.

By "early stage cancer" or "early stage tumor" is meant cancer that is not invasive or not metastatic or is classified as a Stage 0, I, or II cancer.

The term "pre-cancerous" refers to a condition or a growth that typically precedes or develops into a cancer. A "pre-cancerous" growth will have cells that are characterized by abnormal cell cycle regulation, proliferation, or differentiation, which can be determined by markers of cell cycle regulation, cellular proliferation, or differentiation.

Unless stated otherwise, the term "cancer" also encompasses juvenile and non-juvenile cancers, Recurrent and Non-Recurrent cancers as well as cancer relapses.

By "metastasis" is meant the spread of cancer from its primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant.

By "non-metastatic" is meant a cancer that is benign or that remains at the primary site and has not penetrated into the lymphatic or blood vessel system or to tissues other than the primary site. Generally, a non-metastatic cancer is any cancer that is a Stage 0, I, or II cancer.

Reference to a tumor or cancer as a "Stage 0," "Stage I," "Stage II," "Stage III," or "Stage IV" indicates classification of the tumor or cancer using the Overall Stage Grouping or Roman Numeral Staging methods known in the art. Although the actual stage of the cancer is dependent on the type of cancer, in general, a Stage 0 cancer is an in situ lesion, a Stage I cancer is small localized tumor, a Stage II is a local advanced tumor, Stage III cancer is an invasion of lymph nodes or surrounding tissues, and a Stage IV cancer represents metastatic cancer. The specific stages for each type of tumor are known to the skilled clinician.

"Tumor", as used herein, refers to all neoplastic cell growth and proliferation, whether malignant or benign, and all pre-cancerous and cancerous cells and tissues.

By "primary tumor" or "primary cancer" is meant the original cancer and not a metastatic lesion located in another tissue, organ, or location in the subject's body.

"Cancer recurrence" herein refers to a return of cancer following treatment, and includes return of cancer in the primary organ, as well as distant recurrence, where the cancer returns outside of the primary organ.

The compounds of formula (I) as defined above may be useful for treating and/or preventing cancer, in particular for treating and/or preventing solid tumors, especially neuroblastomas, colorectal cancer, androgen-induced bladder cancer, lung cancer, hepatocellular carcinoma, prostate cancer, breast cancer, esophageal cancer and thyroid cancer.

Said autoimmune disorders may induce chronic inflammatory diseases. Herein is provided a group of such inflammatory diseases: inflammatory bowel disease, systemic lupus erythematosus, acute lymphoblastic leukemia of childhood, inflammatory myopathies, and rheumatoid arthritis.

Other autoimmune diseases which may be cited in the framework of the present invention are include Multiple sclerosis (MS), Type 1 diabetes mellitus, Guillain-Barre syndrome, chronic inflammatory demyelinating polyneuropathy and psoriasis.

The compounds of formula (I) as defined above may be useful for treating and/or preventing neurodegenerative diseases, such as, for example, Parkinson's disease, Alzheimer's disease or tauopathies (for example, progressive supranuclear palsy, frontotemporal dementia, corticobasal degeneration or Pick's disease); cerebral traumas, such as ischaemia and cranial traumas and epilepsy; psychiatric diseases, such as schizophrenia, depression, substance dependence or attention deficit hyperactivity disorders; inflammatory diseases of the central nervous system, such as multiple sclerosis, encephalitis, myelitis and encephalomyelitis, and other inflammatory diseases, such as vascular pathologies, atherosclerosis, inflammations of the joints, arthrosis or rheumatoid arthritis; osteoarthritis, Crohn's disease, ulcerative colitis; allergic inflammatory diseases, such as asthma; autoimmune diseases, such as type 1 diabetes, lupus, scleroderma, Guillain-Barré syndrome, Addison's disease and other immune-mediated diseases; osteoporosis; or cancers.

Further described herein are compounds of formula (I) as defined above for use for treating and/or preventing neurodegenerative disorders. Further described herein are compounds of formula (I) as defined above for use, wherein the neurodegenerative disorder is Parkinson's disease. Further described herein are compounds of formula (I) as defined above for use, wherein the neurodegenerative disorder is Alzheimer's disease. Further described herein are compounds of formula (I) as defined above for use, wherein the neurodegenerative disorder is tauopathy.

Further described herein are compounds of formula (I) as defined above for use, wherein the tauopathy is progressive supranuclear palsy. Further described herein are compounds of formula (I) as defined above for use, wherein the tauopathy is frontotemporal dementia. Further described herein are compounds of formula (I) as defined above for use, wherein the tauopathy is corticobasal degeneration. Further described herein are compounds of formula (I) as defined above for use, wherein the tauopathy is Pick's disease.

Further described herein are compounds of formula (I) as defined above for use for treating and/or preventing cerebral traumas. Further described herein are compounds of formula (I) as defined above for use, wherein the cerebral trauma is ischaemia. Further described herein are compounds of formula (I) as defined above for use, wherein the cerebral trauma is cranial traumas. Further described herein are compounds of formula (I) as defined above for use, wherein the cerebral trauma is epilepsy.

Further described herein are compounds of formula (I) as defined above for use for treating and/or preventing psychiatric diseases. Further described herein are compounds of formula (I) as defined above for use, wherein the psychiatric disease is schizophrenia. Further described herein are compounds of formula (I) as defined above for use, wherein the psychiatric disease is depression. Further described herein are compounds of formula (I) as defined above for use, wherein the psychiatric disease is substance dependence. Further described herein are compounds of formula (I) as defined above for use, wherein the psychiatric disease is an attention deficit hyperactivity disorder.

Further described herein are compounds of formula (I) as defined above for use for treating and/or preventing inflammatory diseases of the central nervous system. Further described herein are compounds of formula (I) as defined above for use, wherein the inflammatory disease of the central nervous system is multiple sclerosis. Further described herein are compounds of formula (I) as defined above for use, wherein the inflammatory disease of the central nervous system is encephalitis. Further described herein are compounds of formula (I) as defined above for use, wherein the inflammatory disease of the central nervous system is myelitis. Further described herein are compounds of formula (I) as defined above for use, wherein the inflammatory disease of the central nervous system is encephalomyelitis.

Further described herein are compounds of formula (I) as defined above for use for treating and/or preventing other inflammatory diseases. Further described herein are compounds of formula (I) as defined above for use, wherein the other inflammatory disease is a vascular pathology. Further described herein are compounds of formula (I) as defined above for use, wherein the other inflammatory disease is atherosclerosis. Further described herein are compounds of formula (I) as defined above for use, wherein the other inflammatory disease is an inflammation of the joints. Further described herein are compounds of formula (I) as defined above for use, wherein the other inflammatory disease is arthrosis. Further described herein are compounds of formula (I) as defined above for use, wherein the other inflammatory disease is rheumatoid arthritis. Further described herein are compounds of formula (I) as defined above for use, wherein the other inflammatory disease is osteoarthritis. Further described herein are compounds of formula (I) as defined above for use, wherein the other inflammatory disease is Crohn's disease. Further described herein are compounds of formula (I) as defined above for use, wherein the other inflammatory disease is ulcerative colitis.

Further described herein are compounds of formula (I) as defined above for use for treating and/or preventing osteoporosis.

The compounds of formula (I) as defined above may be useful for treating and/or preventing rheumatoid arthritis, atherosclerosis, diabetes, Parkinson's disease, psychiatric diseases, such as schizophrenia, depression, substance dependence or attention deficit hyperactivity disorders and cancers.

Administration of Compounds of Formula (I)

The compounds of formula (I) as defined here-above may be formulated into a pharmaceutical composition, in particular into a medicament, suitable for administration to a patient.

The present invention thus further relates to a pharmaceutical composition or a medicament comprising a compound of formula (I), or a pharmaceutically acceptable salt thereof.

The present invention also relates to a pharmaceutical composition comprising a compound of formula (I), or any one of their pharmaceutically acceptable salts, and at least one pharmaceutically acceptable excipient, for use in the treatment and/or prevention of autoimmune disorders, cancer, neurodegenerative diseases, cerebral traumas, psychiatric diseases and/or inflammatory diseases, more particularly of cancer.

In particular, the invention relates to a medicament comprising a compound of formula (I) or any one of their pharmaceutically acceptable salts, for use in the treatment and/or prevention of autoimmune disorders, cancer, neurodegenerative diseases, cerebral traumas, psychiatric diseases and/or inflammatory diseases, more particularly of cancer.

Alternatively, the invention relates to the use of a compound of formula (I) as defined above or any one of their pharmaceutically acceptable salts, for the preparation of a pharmaceutical composition or of a medicament for the treatment and/or prevention of autoimmune disorders, cancer, neurodegenerative diseases, cerebral traumas, psychiatric diseases and/or inflammatory diseases, more particularly of cancer.

According to another aspect, herein is provided a method of treating the pathological conditions indicated above, comprising administering to a subject in need thereof a therapeutically effective amount of a compound of formula (I), or a pharmaceutically acceptable salt thereof. In an embodiment of this method of treatment, the subject is a human.

The pharmaceutically acceptable excipient is more particularly chosen among pharmaceutically carrier, adjuvant, or vehicle.

The choice of the acceptable excipient(s) to be used in combination with a compound of formula (I) as defined herein is part of the general knowledge of one having ordinary skills in the formulation of pharmaceutical compositions, in particular of medicaments.

Such excipients are well known to those skilled in the art and are described notably in "*Ullmann's Encyclopedia of Industrial Chemistry, 6th Ed.*" (various editors, 1989-1998 Marchcel Dekker) and in "*Pharmaceutical Dosage Forms and Drug Delivery Systems*" (ANSEL et al, 1994, WILLIAMS & WILKINS).

The aforementioned excipients are selected according to the dosage form and the desired mode of administration.

Compounds and compositions of this invention may be administered in any manner, including, but not limited to, orally, parenterally, sublingually, transdermally, vaginally, rectally, transmucosally, topically, intranasally via inhalation, via buccal or intranasal administration, ophtalmologically or via an implanted reservoir, or combinations thereof. Parenteral administration includes, but is not limited to, intravenous, intra-arterial, intra-peritoneal, subcutaneous, intramuscular, intra-thecal, intra-articular, intra-synovial, intrasternal, intrahepatic, intralesional, intra-tracheal, and intracranial injection or infusion techniques. The compositions of this invention may also be administered in the form of an implant, which allows slow release of the compositions as well as a slow controlled i.v. infusion.

For example, a compound of formula (I) can be present in any pharmaceutical form which is suitable for enteral or parenteral administration, in association with appropriate excipients, for example in the form of plain or coated tablets, hard gelatin, soft shell capsules and other capsules, suppositories, or drinkable, such as suspensions, syrups, or injectable solutions or suspensions.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent. Among the acceptable vehicles and solvents that may be employed are water, Ringer's solution and isotonic sodium chloride solution. In addition, sterile, fixed oils are conventionally employed as a solvent or suspending medium.

Orally acceptable dosage forms include, but are not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In a particular embodiment, a compound of formula (I) according to the invention is administered orally or intravenously Such pharmaceutically acceptable compositions may also be considered in combination with other active compounds, or alternatively may include the compounds according to the invention in combination with other active agents.

The amount of compounds of the present invention that may be combined with the excipient(s) to produce a composition in a single dosage form will vary depending upon the host treated and the particular mode of administration.

In the pharmaceutical compositions for oral, sublingual, subcutaneous, intramuscular, intravenous, topical, local, intra-tracheal, intranasal, transdermal or rectal administration, the compound of formula (I) above, or its base, acid, zwitterion or salt thereof, may be administered in a unit administration form, in a mixture with conventional pharmaceutical excipients, to animals and to human beings for the treatment of the above disorders or diseases.

The unit administration forms appropriate include oral forms such as tablets, soft or hard gel capsules, powders, granules and oral solutions or suspensions, sublingual, buccal, intra-tracheal, intra-ocular and intra-nasal administration forms, forms for inhalative, topical, transdermal, subcutaneous, intra-muscular or intravenous administration, rectal administration forms and implants. For topical application it is possible to use the compounds of formula (I) in creams, gels, ointments or lotions.

As an example, a unit administration form of a compound of formula (I) in tablet form may comprise the following components:

| | |
|---|---|
| Compound of formula (I) | 50.0 mg |
| Mannitol | 223.75 mg |
| Sodium croscarmellose | 6.0 mg |
| Corn starch | 15.0 mg |
| Hydroxypropylmethylcellulose | 2.25 mg |
| Magnesium stearate | 3.0 mg |

There may be particular cases in which higher or lower dosages are appropriate. According to usual practice, the dosage that is appropriate for each patient is determined by the doctor according to the mode of administration and the weight and response of the said patient.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

The following examples are provided as illustrations and in no way limit the scope of this invention.

EXAMPLES

Example 1: Synthesis of 6-[2-(4-fluorophenyl)-4-methyl-imidazo[1,2-b][1,2,4]triazol-5-yl]-1H-indole (1)

1. N-Methoxy-N-methylindole-6-carboxamide (as Described in WO2009/144392 on Page 36)

In a round-bottomed flask, 5.0 g of indole-6-carboxylic acid, 3.3 g of N,O-dimethylhydroxylamine hydrochloride, 11.9 g of 1-(3-dimethylaminopropyl)-3-ethylcarbodiimide and 10 ml of pyridine are placed in 150 ml of tetrahydrofuran. The mixture is stirred at ambient temperature for 40 h. The mixture is concentrated, and the residue is taken up in 150 ml of ethyl acetate and 50 ml of water. The organic phase is washed with 50 ml of a 1N solution of sodium hydroxide and 50 m! of a saturated solution of sodium chloride, dried over magnesium sulphate and then concentrated under reduced pressure. 6.8 g of compound are obtained.

1H NMR ($CDCl_3$, δ in ppm): 3.3 (s, 3H); 3.5 (s, 3H); 6.45 (m, 1H); 7.25 (t, 1H); 7.4 (dd, 1H); 7.55 (d, 1H); 7.75 (s, 1H); 8.8 (s, 1H). M+H=205

2. N-Methoxy-N-methyl-1-(phenylsulphonyl)indole-6-carboxamide (as Described in WO2009/144392 on Page 36)

In a round-bottomed flask, 6.8 g of compound N-Methoxy-N-methylindole-6-carboxamide obtained in step 1 are placed in 100 ml of N,N-dimethylformamide at 0° C. 1.45 g of NaH are added portionwise, followed by 6.52 g of benzenesulphonyl chloride. The mixture is stirred at ambient temperature for 40 h. 150 ml of water are added and the mixture is then extracted with 60 ml of ethyl acetate. The organic phase is washed with 50 ml of a saturated solution of sodium chloride, dried over magnesium sulphate and then concentrated under reduced pressure. The residue is purified by silica gel chromatography, elution being carried out with a heptane/ethyl acetate mixture. 9.5 g of compound are obtained.

1H NMR ($CDCl_3$, δ in ppm): 3.4 (s, 3H); 3.55 (s, 3H); 6.7 (d, 1H); 7.45 to 7.6 (m, 5H); 7.7 (d, 1H); 7.95 (m, 2H); 8.4 (s, 1H). M+H=345.

3. 6-acetyl-1-(phenylsulphonyl)indole (as Described in WO2009/144392 on Page 37)

In a round-bottomed flask, 9.2 g of compound N-Methoxy-N-methyl-1-(phenylsulphonyl)indole-6-carboxamide obtained in step 2 are placed in 250 ml of tetrahydrofuran at 0° C. and under argon. 27 ml of methylmagnesium bromide (3M in diethyl ether) are added dropwise. The mixture is stirred for one hour at 0° C. and 20 h at ambient temperature. The mixture is cooled to 0° C. and 150 ml of water and 50 ml of a saturated solution of ammonium chloride are added. The mixture is extracted with 60 ml of ethyl acetate. The organic phase is washed with 40 ml of a saturated solution of sodium chloride, dried over magnesium sulphate and then concentrated under reduced pressure. 7.3 g of compound are obtained.

1HNMR ($CDCl_3$, δ in ppm): 2.7 (s, 3H); 6.75 (d, 1H); 7.45 to 7.65 (m, 4H); 7.8 (d, 1H); 7.95 (in, 3H); 8.65 (s, 1H). M+H=300; Mp=160-163° C.

4. 2-Bromo-1-[1-(pheny]sulphonyl)indol-6-yl]ethanone (as Described in WO2009/144392 on Page 37)

In a round-bottomed flask, 3 g of copper bromide are placed in 120 ml of ethyl acetate and the mixture is refluxed. 2 g of 6-acetyl-1-(phenylsulphonyl)indole are added. The mixture is stirred for 4 hours at reflux. The mixture is filtered through paper and then the filtrate is poured into 150 ml of a 20% solution of sodium thiosulphate. The mixture is extracted with 60 ml of ethyl acetate. The organic phase is washed with 40 ml of a saturated solution of sodium chloride, dried over magnesium sulphate and then concentrated under reduced pressure. 2.6 g of compound are obtained, 1HNMR ($CDCl_3$, δ in ppm): 4.45 (s, 2H); 6.65 (d, 1H); 7.35 to 7.55 (m, 4H); 7.7 (d, 1H); 7.9 (m, 3H); 8.6 (s, 1H). M+H=378

5. 1-[1-(benzenesulfonyl)indol-6-yl]-2-(3,5-dibromo-1,2,4-triazol-1-yl)ethanone 1.7 g of 3,5-dibromo-1,2,4-triazole and 2.61 ml of diisopropylethylamine are dissolved in 51 ml of dichloromethane and a solution of 2.7 g of 2-bromo-1-[1-(phenylsulphonyl) indol-6-yl]ethanone in 34 ml of dichloromethane are added dropwise. The mixture is stirred for 16 h at room temperature. The mixture is washed with 2×20 ml of water, the organic phase dried over magnesium sulphate and then concentrated under reduced pressure. The residue is purified by silica gel chromatography, elution being carried out with a dichloromethane/ethylacetate mixture. 2.85 g of compound are obtained.

1H NMR (DMSO-$d_6$, δ in ppm): 6.18 (s, 2H); 7.05 (s, 1H); 7.55 to 7.7 (m, 4H); 7.8 (d, 1H); 8.05 (d, 1H); 8.1 (m, 2H); 8.2 (s, 1H); 8.6 (s, 1H). M+H=525

6. 1-(benzenesulfonyl)-6-(2-bromo-4-methyl-imidazo[1,2-b][1,2,4]triazol-5-yl)indole 500 mg of the compound obtained in step 5 are weighed into a tube. 10 ml of toluene are added thereto, followed by 0.60 ml of methylamine solution (8M in ethanol). The tube is sealed and then stirred for 24 h at 140° C. The reaction mixture is cooled to ambient temperature and concentrated under reduced pressure. The residue is taken up in 50 ml of dichloromethane and 20 ml of water. The organique phase is washed with 20 ml of a saturated solution of sodium chloride, dried over magnesium sulphate and then concentrated under reduced pressure. The residue is purified by silica gel chromatography, elution being carried out with a dichloromethane/ethylacetate mixture. 0.134 g of compound are obtained 1H NMR (DMSO-$d_6$, δ in ppm): 3.65 (s, 3H); 6.9 (d, 1H); 7.5 (d, 1H); 7.58 to 7.8 (m, 4H); 7.95 (d, 1H); 8.1 (m, 4H); M+H=457

7. 6-[2-(4-fluorophenyl)-4-methyl-imidazo[1,2-b][1,2,4]triazol-5-yl]-1H-indole

In a reactor, 134 mg of the compound obtained in step 6 are placed in 2 ml of toluene and the mixture is degassed with argon for 10 min. 1.3 mg of palladium acetate, 4.8 mg of 2-dicyclohexylphosphino-2',6'-dimethoxy-1,1'-biphenyl, 125 mg of $K_3PO_4$, 53 mg of 4-fluorophenylboronic acid and a few drops of ethanol are then added. The reaction mixture is heated at 115° C. for 16 h, cooled to ambient temperature and concentrated under reduced pressure. The residue is then purified by silica gel chromatography, elution being carried out with a dichloromethane/methanol mixture. 44 mg of compound are obtained.

1H NMR (DMSO-$d_6$, δ in ppm): 3.72 (s, 3H); 6.55 (m, 1H); 7.25 (m, 1H); 7.32 (m, 2H); 7.48 (m, 1H); 7.62 (s, 1H); 7.72 (d, 1H); 7.85 (s, 1H); 8.12 (m, 2H); 11.35 (s, 1H); M+H=332; MP: 256-258° C.

Example 2: Biological Activity 2.1. Activity on HEK—Nur77 Modulation a) Material and Methods Stable HEK293 cells expressing Gal4-DBD-FL-NOT, -hNur77, -hNOR1 and Pfr-Luc were obtained by limit dilution. HEK cells were grown in 75 $cm^2$ flask in DMEM high glucose 30-2002™ containing 10% calf serum, hygromycin at a content of 250 μg/ml, doxycycline at a content of 2 μg/ml (to induce expression) and 0.4 mg/ml of penicillin. After one week in culture, cells were harvested by trypsinization then plated onto 96 well dishes at the density of 20 000 cell per well in 75 μl of culture medium. After 24 hours compounds were added (25 μl per well) at different concentration for further 24 hours. The medium was removed and measurement was performed by adding 50 μl of Steadyglo (Promega, E2510) with 50 μl PBS per well for 15 minutes and plates were read using microplate luminescent reader.

b) Results

The compound of formula (1) as defined above gave an $IC_{50}$ activity of 0.03 nM.

The compound of formula (2) as defined above gave an $IC_{50}$ activity of 0.1 pM.

The compound of formula (3) as defined above gave an $IC_{50}$ activity of 0.9 nM.

The trifluoroacetate salt of compound of formula (2) as defined above gave an $IC_{50}$ activity of 0.1 pM.

2.2. Activity on Neuroblastomas Cell Lines—Nurr1 Modulation a) Material and Methods N2A cells obtained from ATCC were stably transfected with NBRE8x (50-AAGGTCA-30) in tandem coupled with luciferase reporter gene. Each NBRE sequence was separated with 5 nucleotides. N2A were grown in 75 $cm^2$ flask in DMEM containing 10% calf serum, 4.5 g/L glucose and 0.4 mg/ml geneticin. After one week in culture cells were harvested by trypsinization (0.25%, 30 minutes) then plated onto 96 well dishes at the density of 60 000 cell per well in 75 μl of DMEM without phenol red containing 4.5 g/l glucose, 10% lipid free serum from Hyclone. After 24 hours compounds were added (25 μl/well) at different concentration for further 24 hours. Measurement is performed by adding 100 μl of Steadylite per well for 30 minutes and plates were read using microplate fluorescent reader.

b) Results

The compound of formula (1) as defined above gave an $EC_{50}$ activity of 0.7 nM.

The compound of formula (2) as defined above gave an $EC_{50}$ activity of 63 nM.

The compound of formula (3) as defined above gave an $EC_{50}$ activity of 0.4 nM.

The trifluoroacetate salt of compound of formula (2) as defined above gave an $EC_{50}$ activity of 63 nM.

The invention claimed is:

1. A compound of formula (I) or a pharmaceutically acceptable salt thereof:

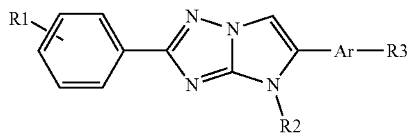

(I)

wherein:

R1 represents a hydrogen atom, a halogen atom, or a $(C_1-C_4)$ hydroxyalkyl group, R2 represents a $(C_1-C_6)$alkyl group, R3 represents a hydrogen atom, a $(C_1-C_4)$alkyl group or a halogen atom, and Ar represents a divalent aromatic ring or a $(C_5-C_{11})$ heteroarylene group.

2. The compound of formula (I) according to claim 1, or a pharmaceutically acceptable salt thereof, wherein:

R1 is a halogen atom or a —$CH_2OH$ group,

R2 and R3 are as defined in claim 1, and

Ar is a phenylene group or an indolylene group.

3. The compound of formula (I) according to claim 1, or a pharmaceutically acceptable salt thereof, wherein:

R2 is a methyl group, and

R3 is a hydrogen atom or a fluorine atom.

4. The compound of formula (I) according to claim 1, or a pharmaceutically acceptable salt thereof, selected from one of the following compounds:

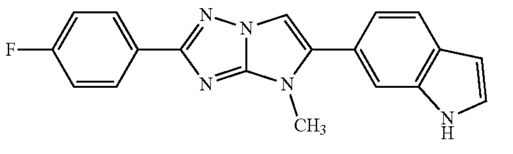

(1)

-continued (2)

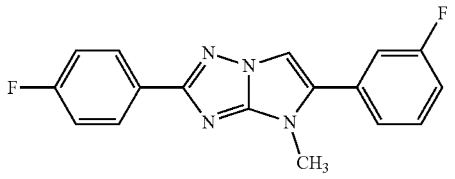

or (3)

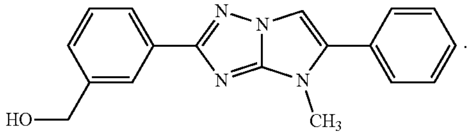

5. A process for preparing the compound of formula (I) according to claim 1, wherein a compound of formula (II)

(II)

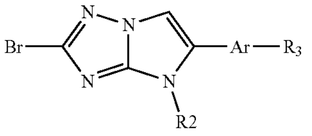

wherein Ar, R2 and R3 are as defined in claim 1 is reacted with a catalyst.

6. A process for preparing a compound of formula (II)

(II)

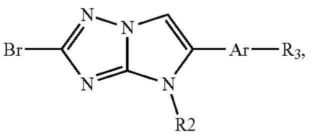

wherein a compound of formula (IV)

(IV)

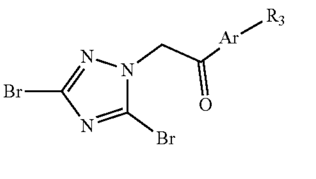

is reacted with an amine of the formula $H_2NR2$, wherein R2 represents a ($C_1$-$C_6$)alkyl group; R3 represents a hydrogen atom, a ($C_1$-$C_4$)alkyl group or a halogen atom; and Ar represents a divalent aromatic ring or a ($C_5$-$C_{11}$) heteroarylene group.

7. A compound selected from compounds of formula (IIa) or (IVa)

(IIa)

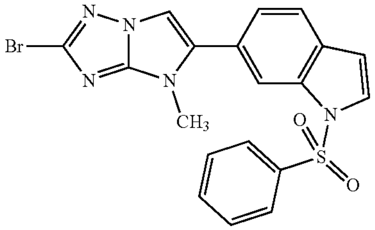

or (IVa)

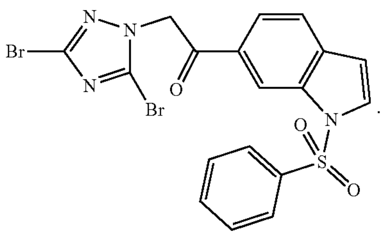

8. A medicament, characterized in that it comprises the compound of formula (I) according to claim 1, or a pharmaceutically acceptable salt thereof.

9. A pharmaceutical composition, characterized in that it comprises the compound of formula (I) according to claim 1, or a pharmaceutically acceptable salt thereof, and at least one pharmaceutically acceptable excipient.

10. A method of preventing and/or treating autoimmune disorders, neurodegenerative diseases, cerebral traumas, psychiatric diseases, inflammatory diseases, and/or cancer, comprising administering to a subject in need thereof the compound of formula (I) according to claim 1, or a pharmaceutically acceptable salt thereof.

11. The method according to claim 10, wherein the cancer is a solid tumor.

12. The compound of formula (I) according to claim 2, wherein R1 is a flourine atom.

13. The compound of formula (I) according to claim 4, wherein the pharmaceutically acceptable salt is a trifluoroacetate salt.

14. The process according to claim 5, wherein the catalyst is a palladium catalyst.

15. The process according to claim 5, wherein the compound of formula (II) is reacted with:

palladium acetate in a solvent in the presence of 2-dicyclohexylphosphino-2',6'-dimethoxy-1,1'-biphenyl, or tetrakis(triphenylphosphin) palladium (0), in acetonitrile and toluene, in the presence of a compound of formula (III)

(III)

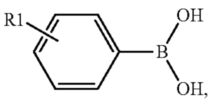

wherein R1 represents a hydrogen atom, a halogen atom, or a ($C_1$-$C_4$) hydroxyalkyl group.

16. The process according to claim 15, wherein the solvent is toluene.

17. The process according to claim 6, wherein the solvent is selected from toluene, benzene, or dichloromethane.

18. The method according to claim 10, wherein the cancer is selected from neuroblastoma, colorectal cancer, androgen-induced bladder cancer, lung cancer, hepatocellular carcinoma, breast cancer, esophageal cancer, or thyroid cancer.

* * * * *